United States Patent [19]

Cerwin et al.

[11] Patent Number: 4,498,476

[45] Date of Patent: Feb. 12, 1985

[54] NON-METALLIC, BIO-COMPATIBLE HEMOSTATIC CLIPS WITH INTERLOCKING LATCH MEANS

[75] Inventors: Robert J. Cerwin, Pittstown, N.J.; Madhusudan Joshi, E. Aurora, N.Y.; John R. Menges, Woodbridge, N.J.; Robert W. Mericle, Lebanon, N.J.; William J. Zwaskis, Carteret, N.J.

[73] Assignee: Ethicon, Inc., Somerville, N.J.

[21] Appl. No.: 552,638

[22] Filed: Nov. 17, 1983

Related U.S. Application Data

[62] Division of Ser. No. 296,672, Aug. 27, 1981, Pat. No. 4,449,531.

[51] Int. Cl.³ .............. A61B 17/00; A61B 17/12
[52] U.S. Cl. .................... 128/346; 128/325; 128/326
[58] Field of Search .............. 128/325, 326, 346

[56] References Cited

U.S. PATENT DOCUMENTS

| | | | |
|---|---|---|---|
| 3,040,749 | 6/1962 | Payton | 128/346 |
| 3,247,852 | 4/1966 | Schneider | 128/346 |
| 3,323,208 | 6/1967 | Hurley, Jr. | 128/346 |
| 3,378,010 | 4/1968 | Codling et al. | 128/346 |
| 3,425,823 | 4/1969 | Edwards | 128/346 |
| 3,706,312 | 12/1972 | Melges | 128/305 |
| 3,735,765 | 5/1973 | Ichelson | 128/335 |
| 3,854,482 | 12/1974 | Laugherty et al. | 128/346 |
| 3,874,042 | 4/1975 | Eddleman et al. | 128/346 |
| 3,973,570 | 8/1976 | Razgulov et al. | 128/346 |
| 4,361,229 | 11/1982 | Mericle | 128/325 |
| 4,434,795 | 3/1984 | Mericle | 128/303 R |

FOREIGN PATENT DOCUMENTS 1957855 7/1973 Fed. Rep. of Germany ...... 128/346

OTHER PUBLICATIONS

Colmed Ltd., Half Moon Bay, CA, "Secuclip" Brochure.

Primary Examiner—C. Fred Rosenbaum
Assistant Examiner—C. W. Shedd
Attorney, Agent, or Firm—Robert L. Minier

[57] ABSTRACT

Sterile, non-metallic, bio-compatible hemostatic clips of absorbable and non-absorbable materials comprising two leg members joined with a resilient hinge. The distal ends of said leg members include latch means to lock the clip in a closed position. Each leg member has a vessel clamping inner face and the latch means includes means for preventing relative lateral movement between the vessel clamping inner faces when the clip is in a closed position.

5 Claims, 8 Drawing Figures

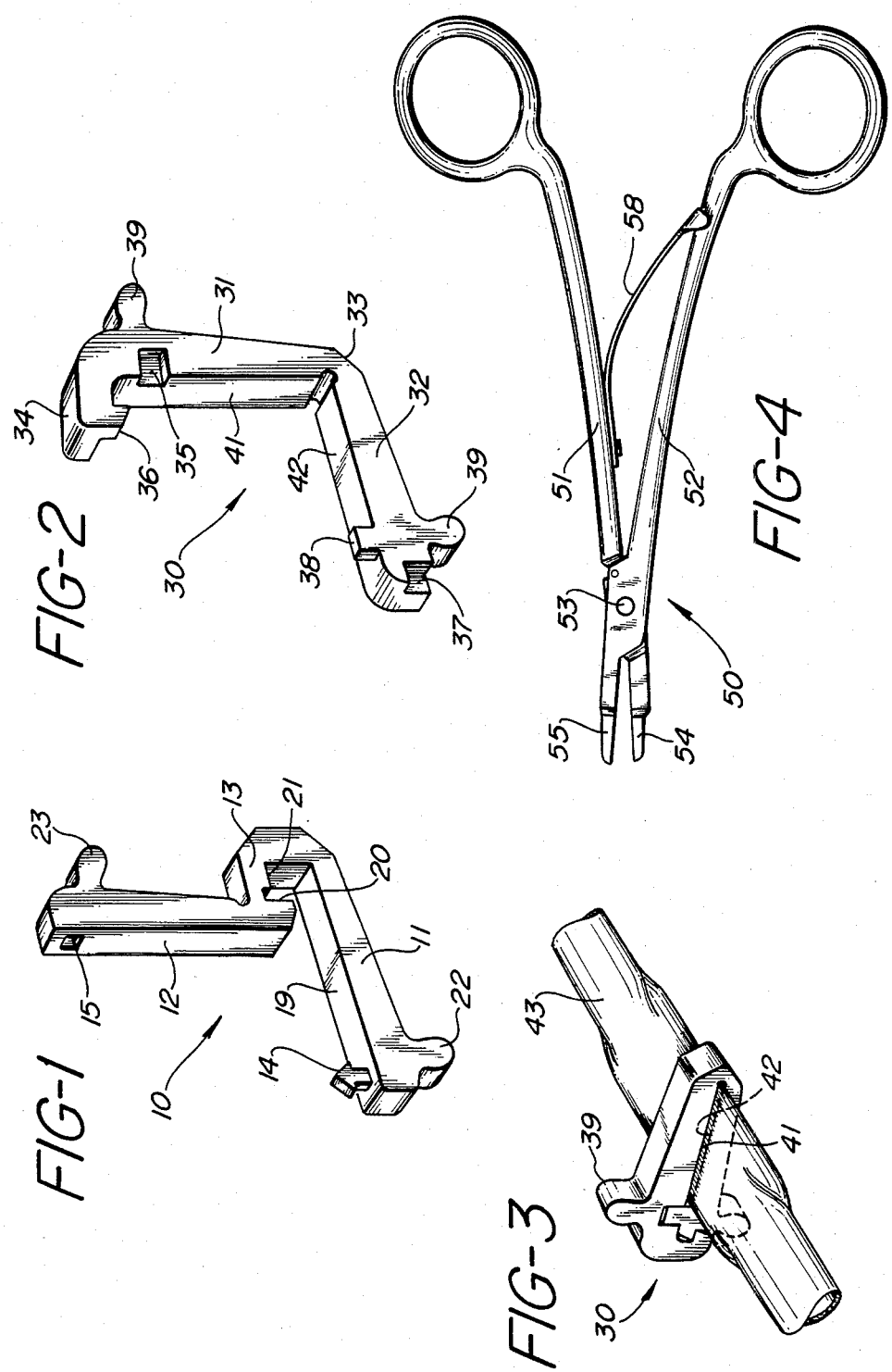

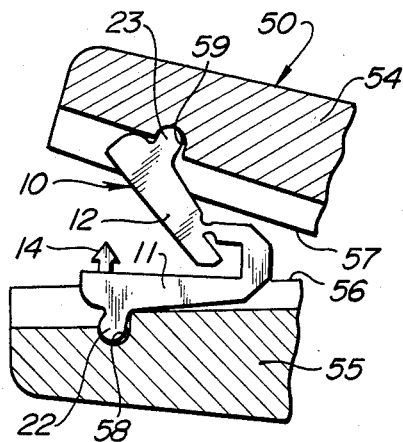
FIG-5
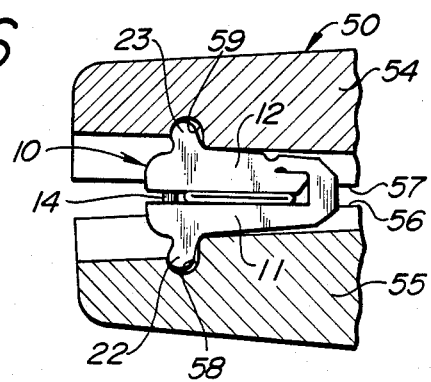
FIG-6
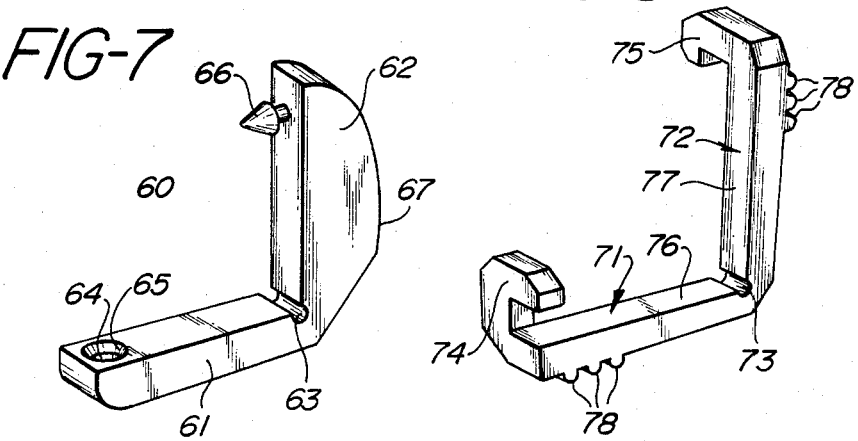
FIG-7
FIG-8

NON-METALLIC, BIO-COMPATIBLE HEMOSTATIC CLIPS WITH INTERLOCKING LATCH MEANS

This is a division of application Ser. No. 296,672, filed Aug. 27, 1981, now U.S. Pat. No. 4,449,531.

The present invention relates to hemostatic clips and clip appliers, and, more particularly, to hemostatic clips fabricated from absorbable or nonabsorbable polymeric materials and to instruments for applying such clips to blood vessels and the like.

BACKGROUND OF THE INVENTION

In many surgical procedures, it is often necessary to ligate a plurality of vessels within the surgical site. The vessels may then be severed downstream of the ligated portion. In some instances, the vessel may be ligated at two areas, spaced from one another, and the portion of the vessel between the ligation removed. The primary reason for ligating the vessels is to maintain the surgical site free of an excess of blood and to reduce blood loss in the patient. Also in certain surgical procedures wherein tumors or parts of organs and the like are to be removed, the tumor or organ may have to be separated from certain vessels which, before separating, will have to be ligated.

Once a blood vessel is completely shut off, hemostasis; that is, the natural closing of the ligated end of the vessel so as to stop blood flow, will occur in about 3 to 5 days. The body, in the meantime, will continue to allow blood to flow around the ligated area through appropriate capillaries and secondary vessels. The natural physiological functions of the body eventually enlarge these by-pass vessels until adequate blood flow is attained. Hence, when ligating the vessel, there should be a positive stopping of the blood flow in the main vessel; i.e., no leakage, which might cause blood loss in the patient and may disrupt the natural hemostasis and concurrent manufacture of new paths of blood flow in the patient.

In the past, this closing of the vessel was usually accomplished using ligatures; i.e., threads or filaments which the surgeon tied around the vessel desired to be closed. This is a very time-consuming process and one in which positive closure of the vessel was not always accomplished.

In relatively recent years hemostatic clips have replaced ligatures in many surgical procedures to close blood vessels and other small fluid ducts. In the past, hemostatic clips have been narrow U-shaped or V-shaped strips formed of tantalum or stainless steel which are capable of being deformed and possess sufficient strength to retain the deformation when clamped about a blood vessel. The clips are generally applied using a forcepstype device having jaws channeled or otherwise adapted to hold the open clip. Representative hemostatic clips and appliers of the prior art are best illustrated in U.S. Pat. Nos. 3,867,944; 3,631,707; 3,439,523; 3,439,522; 3,363,628; 3,312,216; and 3,270,745.

Although the metal hemostatic clips are relatively easy to apply and accomplish a positive closing of the vessel, the metal devices are expensive to manufacture and perhaps, more importantly, disrupt post operative X-ray procedures and subsequent diagnostic imaging procedures. Hence, it is desired that hemostatic clips be made from materials which will not disrupt the postoperative or other subsequent diagnostic procedures, such as X-ray imaging, computerized axial tomography imaging, and the like.

It is critical that hemostatic clips used in surgery be sterilizable by the well known sterilizing techniques; such as, ethylene oxide treatment, cobalt irradiation, and the like without loss in functionality of the clip.

It has been suggested in the prior art, as in U.S. Pat. No. 3,439,523 for example, that hemostatic clips might be formed of inexpensive plastics or materials which are slowly absorbable in the body. Unfortunately, conventional U- and V-shaped hemostatic clips do not possess the required strength or deformability when constructed of known plastic materials to be successfully clamped about a blood vessel. Thus, although the need and desirability of providing inexpensive non-metallic, bio-compatible hemostatic clips of both absorbable and nonabsorbable materials has been recognized for over ten years, there has been no practical way to satisfy this need.

To accomplish the positive closing of the vessel with non-metallic, bio-compatible hemostatic clips, the vessel clamping surfaces of the clips should have substantially no gap between the surfaces when the clip is closed. Also, the surfaces should be sufficiently smooth and have large enough areas so as not to sever or even partially sever the closed vessel. The non-metallic, bio-compatible hemostatic clip, once placed in a clamping position on a vessel, must maintain that position for the period of time required for hemostasis to take place. The clip must maintain its strength in vivo to withstand the pressure trying to force the vessel back open for a sufficient period of time to allow for the natural permanent shutting of the vessel.

The configuration of a hemostatic clip is also important. Because the clip is often used in and around the important organs of the body and the clip is left in the body after the subject surgical procedure is completed, it is important that the clip be configured to keep trauma within the area; i.e., irritation from a foreign object, to a minimum. Smoothness and size of the clip as well as a lack of projections and a minimum of sharp angles all contribute to reducing the trauma which may occur when placing a foreign object such as a hemostatic clip, within a human body.

The clip configuration is also important to insure the proper placement of a clip. When hemostatic clips are used in a surgical procedure, the general practice is for the nurse to pick up the clip in the jaws of a forceps type applying instrument. The nurse passes the instrument with the clip in place to the surgeon. The surgeon places the jaws of the instrument into the surgical site and around the vessel to be ligated. In many instances, the surgeon will be placing the jaws of the instrument into areas where the surgeon has very limited vision. The surgeon then closes the clip over the vessel to be ligated. All of the handling and manipulation of the instrument must be accomplished without dropping the clip and while maintaining the sterility of the clip.

The size of the clip is also important as the smaller the clip, the less foreign material there is being implanted in the patient. Also, the smaller size allows for more clips to be used in a surgical procedure and in certain instances may simplify the procedure or at least reduce possible side effects resulting from the insertion of foreign objects within the human body.

U.S. Pat. No. 3,926,195 describes a plastic clip designed for the temporary or permanent closing of the oviduct and vas deferens in humans. These clips preferably have a clamping surface of from 6 to 10 mm in length and 3 to 6 mm in width. The size of such clips are accordingly considerably larger than is desirable for hemostatic clips. Additionally, clips of U.S. Pat. No. 3,926,195 require the use of several complex tools to apply the clips which are acceptable for the purposes described in the reference but would be unacceptable in a surgical procedure requiring the rapid placement of a large number of hemostatic clips to stem the flow of blood from severed vessels especially when these clips have to be placed in relatively inaccessible areas of the body.

In copending commonly assigned patent applications, Ser. Nos. 49,376, 49,375 and 49,379, all filed June 18, 1979, there are disclosed a number of different types of non-metallic, bio-compatible surgical clips of various configurations. Also, in copending commonly assigned patent application Ser. No. 123,878 filed Feb. 25, 1980, which is incorporated herein by reference, there is disclosed a non-metallic, bio-compatible clip configuration wherein both ends of the clip are mechanically locked in place in the closed position.

Though these clips are suitable for many surgical procedures, they all suffer from the problem that the legs themselves may laterally shift with respect to each other so that their vessel clamping surfaces are not disposed fully flush with respect to each other which may allow the locking end of the clip to open. This problem increases the smaller the width of the clip and the longer the clip legs.

While the importance of the clip to the surgical procedure has been discussed, it should be pointed out that the configuration of the clip is also important to the manufacture of the clip. The configuration should be such as to take advantage of simple and economic means of manufacture of the clip such as injection molding. The configuration should be such as to reduce the production of seconds or malformed clips during manufacture. Also, the configuration of the clip should be such as to allow for very simple design of the applier while maintaining the required assurance of holding and setting the clip during the surgical procedure.

It is accordingly an object of the present invention to provide sterile, non-metallic, bio-compatible hemostatic clips effective for clamping off small blood vessels and other fluid ducts in the body. It is a further object of this invention to provide sterile non-metallic, bio-compatible hemostatic clips of both absorbable and nonabsorbable materials. It is yet a further object of this invention to provide sterile, non-metallic, biocompatible ligating clips which are quickly and easily applied to severed blood vessels and other fluid ducts with a single forceps-type instrument such as those used in applying metallic clips. It is yet a further object of this invention to provide non-metallic, bio-compatible ligating clips which are securely locked in place to prevent their vessel clamping surfaces from moving laterally with respect to each other when the clip is in the closed position.

SUMMARY OF THE PRESENT INVENTION

The hemostatic clips of the present invention comprise two leg members joined at the proximal ends thereof along a line forming a resilient hinge, with the first leg member, having at its distal end, a latch means adapted to engage a complementing latch means at the distal end of the second leg member. Each leg member has a vessel clamping inner face in opposition to a vessel clamping inner face of the other leg member. The latching means includes means to prevent relative lateral movement between the clamping inner faces when the clip is in the closed position. Each leg member also includes applier gripping means disposed on its outer surface for use in holding and closing the clip during its application.

The applier for the clips of the present invention is a forceps-type instrument wherein each jaw is channeled to receive the width and length of the clip and accept the applier gripping means on the outer surface of the legs of the clip.

In a preferred embodiment of the clip of the present invention, the proximal ends of the leg members containing the hinge section are constructed so as to mechanically lock at this end when the clip is closed.

The clips may be formed of various polymers by injection molding or other suitable technique, and may be composed of a nonabsorbable material such as polypropylene or an absorbable material such as a homopolymer or copolymer of lactide and glycolide and p-dioxanone. The clips are formed in a normally open position and constructed with a small amount of material to minimize tissue reaction. The clips are readily applied with a forceps-type applier using conventional surgical techniques.

DESCRIPTION OF DRAWINGS

FIG. 1 is a greatly enlarged view in perspective of one embodiment of a surgical clip according to the present invention.

FIG. 2 is a greatly enlarged view in perspective of another embodiment of a surgical clip according to the present invention.

FIG. 3 illustrates the clip of FIG. 2 clamped about a blood vessel.

FIG. 4 illustrates a forceps-type applier useful with the clips of the present invention.

FIG. 5 illustrates the open clip of FIG. 1 retained in the jaws of a forceps-type clip applier.

FIG. 6 illustrates the clip of FIG. 1 closed and locked over a blood vessel in the jaws of the applier.

FIG. 7 is an enlarged perspective view of another embodiment of an interlocking clip of the present invention.

FIG. 8 is an enlarged perspective view of yet another embodiment of an interlocking clip of the present invention.

DESCRIPTION OF PREFERRED EMBODIMENTS

Referring to FIG. 1, there is illustrated a hemostatic clip 10 constructed of two leg members 11 and 12 connected at the proximal ends thereof by a hinged section 13. One leg member 11 has disposed at its distal end a protrusion 14 while the opposite leg member 12 has disposed, at its distal end, a recess 15 for accepting the protrusion. The vessel clamping inner face 16 of the second leg member 12 is disposed in opposed relationship to the vessel clamping inner face 19 of the opposite or first leg member 11. In this embodiment, the hinged area is constructed so that in closing, the surface 20 of the second leg member 12 pivots at the hinge and is locked under the surface 21. This structure provides for a mechanical locking of leg 12 when the clip is in a closed position. This feature becomes important with biologically absorbable materials in that this mechanical lock maintains the hinge end closed for an extended period during the absorption process.

The leg member 12 of the clip includes a boss 23 extending across the width of the leg member near at the distal end thereof. The leg member 11 of the clip also includes a boss 22 extending across the width of the leg member near the distal end thereof. These bosses are constructed so as to engage complimentary recesses in forceps to retain and control the clip while it is being applied.

The bosses are generally cylindrical in construction so as to distribute the forces, and rotate journal like during the closing of the clip. The bosses are spaced from the hinge area and positioned close to the latch area to provide adequate leverage in the closing of the clip about a vessel.

It is preferred that the proximal ends of leg members 11 and 12 be slightly tapered being smaller at hinge section 13. This feature provides flexure of the leg member over tissue. This feature also provides a relief area or gap between this area and the clip applying instrument so that the clip closing forces are applied preferentially to the portion of the clip carrying the bosses.

Referring to FIG. 2, there is shown another embodiment of a hemostatic clip 30 in accordance with the present invention. In this embodiment, the leg members 31 and 32 are connected at their proximal end by hinged section 33.

One leg member 31 includes a curved section 34 at its distal end.

At the beginning of the curved section 34, there is a recessed area 35 and the curved section terminates in protrusion 36. The opposite leg member 32 terminates in a recessed area 37 configured to accept the protrusion 36. This leg member 32 also carries a protrusion 38 adapted to fit into the recessed area 35 of the opposite leg member. Each leg member carries on its outer surface a boss 39 for use in retaining and applying the clip to close off a blood vessel. When the vessel clamping inner face 41 of leg member 31 is urged toward the vessel clamping inner face 42 of leg member 32 and when the clamping faces are adjacent each other protrusion 36 will fit into the recess 37 and protrusion 38 will fit into recess 35 and will prevent relative lateral movement between the clamping faces.

FIG. 3 depicts the clip shown in FIG. 2 in position about a blood vessel with the vessel clamping inner faces 41 and 42 of the clip 30 closing off the vessel 43.

FIG. 4 illustrates a forceps-type hemostatic clip applier 50 comprising two handle members 51 and 52 crossing at hinge point 53 and maintained in a normally open position by spring 58. Handle 51 extends beyond hinge 53 forming jaw member 54 while the extension of handle 52 forms jaw member 55.

FIG. 5 illustrates the detail of the construction of jaws 54 and 55 and the interaction of the jaws with the clip of FIG. 1. Jaws 54 and 55 are of identical design and are provided respectively with channels 56 and 57 extending rearwardly from the tips of the jaws. Each channel is provided with a cylindrical recess 58 and 59 respectively across the width of the channel and near the distal end thereof. Recesses 58 and 59 are in alignment when the jaws of the applier are closed and are sized to receive the cylindrical bosses 22 and 23 of the clip. Channels 56 and 57 forward of recesses 58 and 59 are deeper than to the rear of the recesses as illustrated in FIG. 5. When the open clip is held in the applier, the bosses on the clip are received by the recesses in each jaw. Due to the angle of the clip in the applier, the distal ends of legs 11 and 12 extend into the deeper forward channel section of each jaw.

The clip is molded with a larger internal angle than is shown in FIG. 5 when the clip is in the applier. This feature uses the resilient hinge as a flexible spring to seat the bosses into the recesses in the applier jaws. As the hinge flexes, a spring action follows such that if the applier is closed and opened a small amount, the clip will not fall out of the applier. This overcomes a substantial problem with the metal clip of the prior art which have a considerable tendency to fall out of the jaws of the applier if there is slight flexing of the applier during handling.

Clip 10 is initially loaded in applier 50 in the open position as illustrated in FIG. 5. After moving the jaws of the applier and the clip into position over the vessel to be ligated, the jaws of the applier are closed and the clip is locked in position over the vessel 59 as illustrated in FIG. 6. As the clip is closed, the cylindrical bosses of legs 11 and 12 are rotably engaged by the cylindrical recesses of jaws 57 and 56 and maintained in position in the by the hinge spring force applier until the protrusion 14 of leg member 11 is positioned within and held by the recess 15 in leg member 12. After the clip has been securely latched over the vessel to be ligated, the jaws of the applier are opened to release the clip and vessel and a new clip is loaded in the applier. Since the jaws of the applier are identical, it is not necessary to orient the applier to the clip when loading the applier.

It should be pointed out that the cylindrical bosses on the clip and the complementary cylindrical recesses in the applying instrument are important to allow for positive gripping and closing of the clip. As may be seen in FIGS. 5 and 6 the leg members of the clip move through an angle of about 75° when the clip is closed while the jaws of the instrument only move through an angle of about 5° to 10°. Hence, the applying gripping means on the clip must be free to rotate in the jaws of the applying instrument as the clip is being closed.

Referring to FIG. 7, there is illustrated a hemostatic clip 60 constructed of two leg members 61 and 62 connected at the proximal ends thereof by a hinged section 63. The one leg member 61 terminates at its distal end in a recessed area 64 having a flexible flange 65 disposed about the periphery of the area. The flange may partially close the recessed area or it may entirely close the recessed area and be cut to provide for deflection. The second leg member 62 has disposed about its inner surface at the distal end of the member a protrusion 66. The protrusion is conical in shape and is sized to snugly fit into the recessed area of the other leg member 61. A substantial portion of the outer surface 67 of the leg member 62 defines a curve of substantially constant radius extending from its outer end. The effect of this curvature is to permit the clip to slide forward and rotate during closure. The curvature also reduces the thickness of the leg at the distal end thereof. The clip as described in FIG. 7 is more fully described as to the shape and curvature of its outer surfaces and the manner in which it is used and applied with specific forceps in copending commonly assigned patent application Ser. No. 49,376 filed June 18, 1979.

As may be seen from both FIG. 1 and FIG. 7, when the clip is in the closed position and the protrusion gripped by the recess, the configuration of the protrusion and the recess prevents lateral movement between the vessel clamping inner faces.

FIG. 8 shows still another embodiment of a hemostatic clip in accordance with the present invention. In this embodiment the clip 70 comprises a pair of leg members 71 and 72 connected at their proximal ends by a resilient hinge section 73. The distal end of leg member 71 terminates in a vertically protruding hook section 74 and the distal end of leg member 72 terminates in a horizontally extending hook section 75. The hook sections have complimentary configurations which interlock with each other when the clip is closed and present lateral movement between the vessel clamping inner faces 76 and 77. The outer surface of each leg member carries a plurality of ridges 18 as the gripper applying means. These ridges cooperate with a complementary plurality of grooves disposed in the jaws of the forceps type applying instrument.

Many variations in the clip design other than the embodiments disclosed herein will be apparent to those skilled in the art and are contemplated within the scope of the present invention.

The clips of the present invention may be constructed in various sizes according to their intended function. Hemostatic clips are typically less than 6 mm in length, about 1.5 mm in width, and have a vessel clamping surface about 3 mm in length. The dimensions of the clip may be reduced by about 50 percent for certain applications in microsurgery. Larger clips for special hemostatic applications and other functions such as closure of oviducts or vas deferens may have dimensions of about double those of a typical hemostatic clip. The various sizes of clips are preferably matched with individual appliers having jaws tailored to the size of the clip for best performance.

The clips of the present invention are most conveniently molded of biologically acceptable non-metallic materials which may be absorbable or nonabsorbable. Preferred absorbable polymers include homopolymers and copolymers of glycolide and lactide, and p-dioxanone. Preferred nonabsorbable polymers include nylon and polypropylene. All these materials have been demonstrated to be biologically acceptable when used as sutures or other implantable medical devices. The clips may also be cast or machined from solid polymeric materials.

Having now described the invention in considerable detail, it should be readily apparent to those skilled in the art that various modifications and alterations may be made to the invention without departing from the spirit and scope thereof.

We claim:

1. A hemostatic clip comprising first and second leg members, each member having an elongated vessel clamping inner face in opposition to a vessel clamping inner face of the other leg member, said first leg member terminating at its proximal end in a bend forming a hooked member extending from said vessel clamping inner face, said second leg member terminating at its proximal end in a configuration adapted for engagement by said hooked member of said first leg member, hinge means joining said first and second leg members adjacent said proximal ends, said first and second leg members being rotatable about said hinge means from an open position to a closed position, said leg members terminating at their distal ends in latch means including means for preventing relative lateral movement between vessel clamping inner faces of the leg members when the clip is in the closed position.

2. The hemostatic clip according to claim 1 wherein said first and second leg members include applier gripping means disposed on the outer surfaces of the leg members at the distal ends thereof.

3. The hemostatic clip according to claim 1 or 2 wherein the latch means disposed at the distal ends of the leg members comprises a protrusion and a recess at the distal end of each leg member, said protrusion being disposed from the distal end of one leg member so as to interlock with the recess disposed in the distal end of the other leg member whereby relative movement between the vessel clamping inner faces of the leg members is prevented when the clip is in the closed position.

4. The hemostatic clip according to claim 1 or 2 wherein the latch means disposed at the distal ends of the leg members comprises a protrusion disposed from an extension of the vessel clamping inner face of one leg member and a recess disposed in an extension of the vessel clamping inner face of the other leg member, said protrusion and recess being configured to prevent lateral movement between the vessel clamping inner faces when the clip is in the closed position.

5. A clip of claim 1 wherein said applier gripping means comprises at least one generally cylindrical boss disposed on the outer surface of each leg member, said boss extending across the width of said leg member.

* * * * *